United States Patent
Gale et al.

(10) Patent No.: US 11,446,142 B2
(45) Date of Patent: Sep. 20, 2022

(54) COLLAPSIBLE LEAFLETS FOR PROSTHETIC HEART VALVES

(71) Applicant: St. Jude Medical, Cardiology Division, Inc., St. Paul, MN (US)

(72) Inventors: Caytlin Gale, Minneapolis, MN (US); Gary Erzberger, Plymouth, MN (US); Kristen T. Morin, St. Paul, MN (US); Trevor J. Springer, Stillwater, MN (US); Jaron J. Olsoe, Minneapolis, MN (US); Kristopher Henry Vietmeier, Monticello, MN (US); Julia K. Roe, Stoughton, WI (US); Hannah Mitchell, Anchorage, AK (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 135 days.

(21) Appl. No.: 17/022,181

(22) Filed: Sep. 16, 2020

(65) Prior Publication Data
US 2021/0077254 A1 Mar. 18, 2021

Related U.S. Application Data

(60) Provisional application No. 62/902,044, filed on Sep. 18, 2019.

(51) Int. Cl.
*A61F 2/24* (2006.01)

(52) U.S. Cl.
CPC .......... *A61F 2/2418* (2013.01); *A61F 2/2409* (2013.01); *A61F 2/2412* (2013.01); *A61F 2/2415* (2013.01); *A61F 2220/0075* (2013.01)

(58) Field of Classification Search
CPC .... A61F 2/2403; A61F 2/2412; A61F 2/2415; A61F 2/2418
See application file for complete search history.

(56) References Cited

U.S. PATENT DOCUMENTS

| | | | | |
|---|---|---|---|---|
| 3,861,416 A | * | 1/1975 | Wichterle | A61F 2/2403 137/849 |
| 10,143,551 B2 | | 12/2018 | Braido et al. | |
| 2006/0235511 A1 | * | 10/2006 | Osborne | A61F 2/2418 623/2.12 |
| 2009/0041978 A1 | * | 2/2009 | Sogard | A61L 31/121 428/137 |
| 2015/0173899 A1 | * | 6/2015 | Braido | A61F 2/2445 623/2.38 |

* cited by examiner

*Primary Examiner* — Suba Ganesan
(74) *Attorney, Agent, or Firm* — Wei & Sleman LLP

(57) ABSTRACT

A prosthetic heart valve may include a collapsible and expandable stent, a cuff attached to an annulus section of the stent, and a plurality of leaflets attached to at least one of the cuff or the stent within an interior region of the stent. The stent may have a plurality of cells connected to one another in a plurality of annular rows around the stent. The leaflets together may have a coapted position occluding the interior region of the stent and an open position in which the interior region is not occluded. Each leaflet may include a flat mesh of braided wire material having a plurality of pores extending therethrough. The leaflets may be devoid of biological material at a time of implantation.

20 Claims, 1 Drawing Sheet

COLLAPSIBLE LEAFLETS FOR PROSTHETIC HEART VALVES

CROSS-REFERENCE TO RELATED APPLICATIONS

This application claims the benefit of the filing date of U.S. Provisional Patent Application No. 62/902,044, filed Sep. 18, 2019, the disclosure of which is hereby incorporated herein by reference.

BACKGROUND OF THE INVENTION

The present disclosure relates in general to heart valve replacement and, in particular, to prosthetic heart valves. More particularly, the present disclosure relates to leaflets for use in prosthetic heart valves.

Open-heart and transcatheter heart valve replacements are increasingly being performed in lower-risk patients. Such patients are typically younger than the higher-risk patient population that has traditionally received prosthetic heart valves, so they have a longer remaining life expectancy than traditional prosthetic heart valve recipients.

Rigid mechanical heart valves may be sutured into a native annulus of a patient during an open-heart surgical procedure, for example. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to rigid mechanical heart valves and collapsible prosthetic heart valves, conventional prosthetic heart valves suffer from some shortcomings. For example, in conventional collapsible prosthetic heart valves, the leaflets are typically made from biological tissue, such as porcine tissue. Over an extended patient lifespan, such biological leaflets may eventually erode or tear, creating a need for further surgical intervention or an additional valve replacement.

There therefore is a need for further improvements to rigid mechanical heart valves and collapsible prosthetic heart valves. Among other advantages, the present invention may address one or more of these needs.

BRIEF SUMMARY OF THE INVENTION

The disclosure herein describes multiple embodiments of a prosthetic heart valve, including surgically implanted mechanical heart valves and transcatheter heart valves. A prosthetic heart valve may include a collapsible and expandable stent having a proximal end, a distal end, an annulus section adjacent the proximal end, and a plurality of cells connected to one another in a plurality of annular rows around the stent; a cuff attached to the annulus section of the stent; and a plurality of leaflets attached to at least one of the cuff or the stent within an interior region of the stent, the leaflets together may have a coapted position occluding the interior region of the stent and an open position in which the interior region is not occluded, each leaflet may include a flat mesh of braided metal material having a plurality of pores extending therethrough, and the leaflets may be devoid of biological material at a time of implantation.

Also described herein are multiple embodiments of a prosthetic heart valve that may include a collapsible and expandable stent having a proximal end, a distal end, an annulus section adjacent the proximal end, and a plurality of cells connected to one another in a plurality of annular rows around the stent; a cuff attached to the annulus section of the stent; and a plurality of leaflets attached to at least one of the cuff or the stent within an interior region of the stent, the leaflets together may have a coapted position occluding the interior region of the stent and an open position in which the interior region is not occluded, each leaflet may include a wire frame defining a periphery of the leaflet and a central flexible body affixed to the frame, the flexible body may have a plurality of pores extending therethrough, and the leaflets may be devoid of biological material at a time of implantation.

Further described herein are multiple embodiments of a mechanical heart valve that may include a frame defining a central opening; a sewing cuff affixed to and extending around an exterior periphery of the frame; and one or more leaflets each pivotably coupled to the frame, the leaflets together may have a closed position substantially occluding the central opening and an open position in which the central opening may not be substantially occluded, each leaflet may include a flat mesh of braided wire material having a plurality of pores extending therethrough, and the leaflets may be devoid of biological material at a time of implantation.

Still further described herein are multiple embodiments of a mechanical heart valve that may include a frame defining a central opening; a sewing cuff affixed to and extending around an exterior periphery of the frame; and one or more leaflets each pivotably coupled to the frame, the leaflets together may have a closed position substantially occluding the central opening and an open position in which the central opening may not be substantially occluded, each leaflet may include a wire frame defining a periphery of the leaflet and a central flexible body affixed to the frame, the body may have a plurality of pores extending therethrough, and the leaflets may be devoid of biological material at a time of implantation.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. Also as used herein, the terms "generally," "substantially," "approximately," and "about" are intended to mean that slight deviations from absolute are included within the scope of the term so modified.

When used to indicate relative locations within the prosthetic heart valve, the terms "longitudinal" and "vertical" are to be taken as the direction of the axis extending between the proximal end and the distal end of the stent of the heart valve, along the direction of intended blood flow; the term "flow direction" is to be taken as the direction from the proximal end to the distal end of the stent of the heart valve; and the terms "above," "below," "high," and "low" are to be taken as relative to the proximal end of the stent. "Above" and "high" are to be understood as relatively farther from the proximal end of the stent in the direction of intended blood flow, and "below" and "low" are to be understood as relatively closer to the proximal end of the stent in the direction of intended blood flow. When used to indicate relative locations within the prosthetic heart valve, the term "circumferential" is to be taken as the direction of rotation about the longitudinal axis of the stent.

Figure 1:
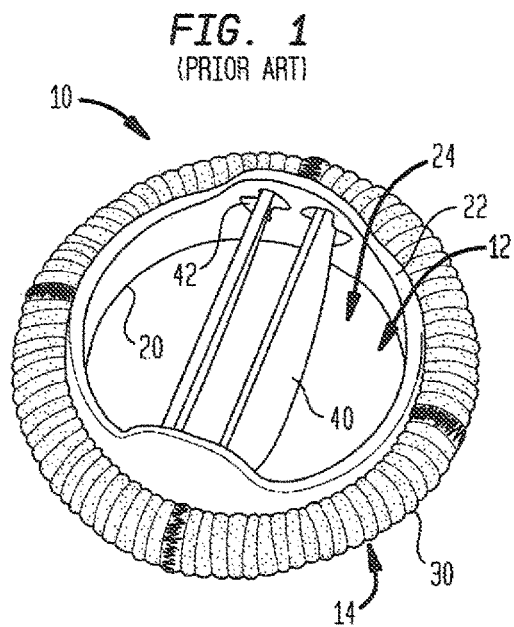
FIG. 1 is a perspective view of a conventional mechanical heart valve.

FIG. 1 illustrates a conventional mechanical heart valve 10 ("MHV") that may be configured to be implanted into a patient to replace a native heart valve that may be malfunctioning, such as the aortic valve, mitral valve, pulmonary valve, or the tricuspid valve. The MHV 10 may be sutured into a native valve annulus of a patient during an open-heart surgical procedure, for example. The MHV 10 may have a rigid frame 20, a sewing cuff 30 affixed to and extending around an exterior periphery 22 of the frame, and two leaflets 40 pivotably coupled to the frame by hinges 42. The frame 20 may be made of a rigid biocompatible material, such as rigid pyrolytic carbon, for example. The sewing cuff 30 is configured to be sutured into the native annulus of the patient.

The leaflets 40 are configured to move between the open position shown in FIG. 1 and a closed position in which the leaflets are rotated about the hinges 42 so that the leaflets occlude a central opening 24 of the frame 20. The leaflets 40 are configured such that they are in the open position when an inflow pressure on an inflow side 12 of the MHV 10 is greater than an outflow pressure on an outflow side 14 of the MHV, and such that they are in the closed position when the outflow pressure is greater than the inflow pressure. The leaflets 40 are typically made of a metal or ceramic plate that is impermeable to liquid.

Figure 2A:
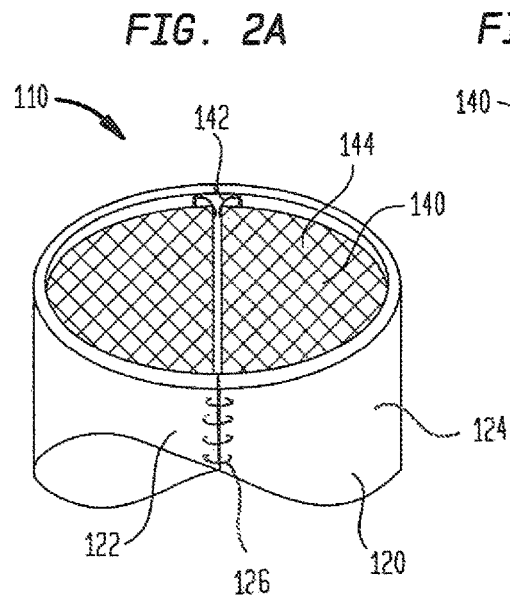
FIG. 2A is a perspective view of a portion of a mechanical heart valve, according to one embodiment of the present invention.

FIG. 2A illustrates a mechanical heart valve 110 ("MHV") according to an embodiment of the invention that may be configured to be inserted into a patient to replace a native heart valve that may be malfunctioning, in a similar manner as the MHV 10. The MHV 110 may function in a similar manner as the MHV 10. The MHV 110 may have a rigid frame 120, a sewing cuff (not shown) affixed to and extending around an exterior periphery 122 of the frame, and two leaflets 140 pivotably coupled to the frame by hinges 142. The frame 120 may be made of any rigid biocompatible material. In one embodiment, the frame 120 may be made of rigid pyrolytic carbon.

The leaflets 140 may include a braided metal material, in which a metal wire, such as a wire formed from the nickel-titanium alloy known as nitinol, is braided to create a flat mesh. The metal wire may have a diameter of between about 0.002 inches and about 0.020 inches. The metal wire may be arranged in a flat mesh pattern having a plurality of pores 144 between locations where the wires overlap one another. After the MHV 110 is implanted into the native valve annulus of a patient, the leaflets 140 would initially allow blood flow through the pores 144, but the leaflets may be configured such that the pores would be closed within seconds or minutes of implantation via acute clotting within the pores. Over time, this initial healing response would be converted into an endothelialized layer of tissue within the pores. In some examples, the leaflets 140 may include a braded wire material that is not made of metal, but that has rigidity similar to that of a metal wire. Other materials may be used, but it is desirable that such materials should exhibit superelasticity in order to effectively collapse the leaflets into a delivery device.

The leaflets 140 may comprise two layers of braided wire with a layer of fabric between the layers of braided wire. The wire may be nitinol and the fabric may be made of a polyester material, for example. The presence of the fabric layer may help promote occlusion of the pores 144 to speed the formation of the endothelialized layer of tissue. In one embodiment, the layers of braided nitinol and the layer of fabric may be combined by placing the layer of fabric in a tube of braided nitinol, flattening the tube around the layer of fabric using heat-set forming fixtures, for example, and then trimming the nitinol/fabric assembly to the desired shape. In some examples, the leaflets 140 may include an inner layer of material that is not made of fabric, but that has flexibility similar to that of a fabric, such as a polyurethane sheet.

Figure 2B:
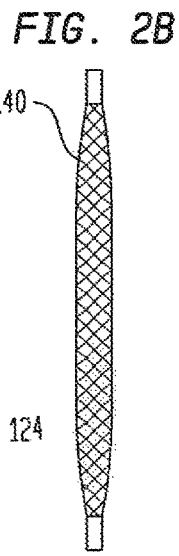
FIG. 2B is a plan view of one of the leaflets of the mechanical heart valve of FIG. 2A, shown in a collapsed condition.

In one embodiment, MHV 110 may be collapsible, such that the MHV may be delivered into the native annulus of a patient in a collapsed condition using a transcatheter delivery device, and may then be released from the delivery device and moved to an expanded condition. The leaflets 140 may each be compressed into the collapsed position shown in FIG. 2B, so that they may fit into the delivery device. In order to collapse the MHV 110, the frame 120 would also need to be collapsible. In such an example, the frame 120 could be made of a segmented material, such as segmented pyrolytic carbon, and the segments 124 could be coupled to one another with metal wiring 126, such as a nitinol wire. The leaflets 140 may be coupled to the frame 120 with sutures, such that after the frame and the leaflets are released from the delivery device and moved to the expanded condition, the frame and the leaflets will move to the arrangement shown in FIG. 2A.

Figure 3:
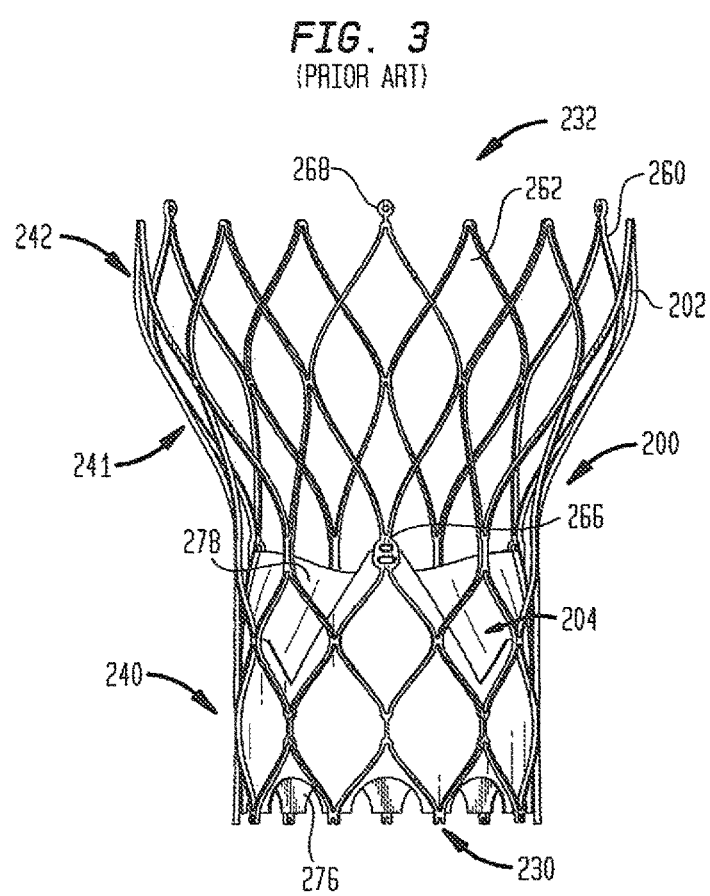
FIG. 3 is a side view of a conventional collapsible prosthetic heart valve.

Braided metal leaflets such as the leaflets 140 described above may also be used in connection with collapsible prosthetic heart valves such as that shown in FIG. 3. FIG. 3 illustrates a collapsible stent-supported prosthetic heart valve 200 including a stent 202 and a valve assembly 204 as is known in the art. The prosthetic heart valve 200 is designed to replace a native heart valve of a patient, such as a native aortic valve. It should be noted that while the example of FIG. 3 is described as a prosthetic aortic valve having a stent with a shape as illustrated, the valve could be a bicuspid valve, such as the mitral valve, and the stent could have different shapes, such as a flared or conical annulus section, a less-bulbous aortic section, and the like, and a differently shaped transition section. Any details of the structure and function of the prosthetic heart valve 200 that are not described herein may be found in U.S. Pat. No. 10,143,551, the entire disclosure of which is hereby incorporated by reference herein.

The stent 202 may be formed from biocompatible materials that are capable of self-expansion or expansion via a balloon, including, for example, shape memory alloys such as nitinol, or other suitable metals or polymers. The stent 202 extends from a proximal or annulus end 230 to a distal or aortic end 232, and includes an annulus section 240 adjacent the proximal end, a transition section 241, and an aortic section 242 adjacent the distal end. Each of the sections of stent 202 includes a plurality of struts 260 forming cells 262 connected to one another in one or more annular rows around the stent. For example, as shown in FIG. 3, the annulus section 240 may have two annular rows of complete cells 262 and the aortic section 242 and the transition section 241 may each have one or more annular rows of partial cells. The stent 202 may include one or more retaining elements 268 at the distal end 232, the retaining elements being sized and shaped to cooperate with female retaining structures (not shown) provided within a transcatheter delivery device.

The prosthetic heart valve 200 includes the valve assembly 204 preferably positioned in the annulus section 240 of the stent 202 and secured to the stent. The valve assembly 204 includes a cuff 276 and a plurality of leaflets 278 that collectively function as a one-way valve by coapting with one another. As a prosthetic aortic valve, the prosthetic heart valve 200 has three leaflets 278. However, it will be appreciated that other prosthetic heart valves with which the leaflets of the present disclosure may be used may have a greater or lesser number of leaflets. Both the cuff 276 and the leaflets 278 may be wholly or partly formed of any suitable biological material or polymer such as, for example, polytetrafluoroethylene (PTFE), polyvinyl alcohol (PVA), ultra-high molecular weight polyethylene (UHMWPE), silicone, urethane, and the like.

The leaflets 278 may be attached along their belly portions to the cells 262 of the stent 202, with the commissure between adjacent leaflets being attached to commissure attachment features 266. As can be seen in FIG. 3, each commissure attachment feature 266 may lie at the intersection of four cells 262, two of the cells being adjacent one another in the same annular row, and the other two cells being in different annular rows and lying in end-to-end relationship. Each of the commissure attachment features 266 may include one or more eyelets that facilitate the suturing of the leaflet commissure to the stent 202.

The prosthetic heart valve 200 may be used to replace a native aortic valve, a surgical heart valve, a heart valve that has undergone a surgical procedure, or any other valve that it is desired to replace. The prosthetic heart valve 200 may be delivered to the desired site (e.g., near or proximate a native valve annulus, or near or proximate an annuloplasty ring or other repair device) using any suitable delivery device.

During delivery, the prosthetic heart valve 200 may be disposed inside a transcatheter delivery device in a collapsed condition. The delivery device may be introduced into a patient using a transfemoral, transapical, transseptal, transradial, transsubclavian, transaortic or any other percutaneous approach. Once the delivery device has reached the target site, the user may deploy the prosthetic heart valve 200. Upon deployment, the prosthetic heart valve 200 expands so that the annulus section 240 is in secure engagement within the native valve annulus (or in engagement with an annuloplasty ring or other repair device). When the prosthetic heart valve 200 is properly positioned, it works as a one-way valve, allowing blood to flow in a flow direction, and preventing blood from flowing in the opposite direction.

Figure 4:
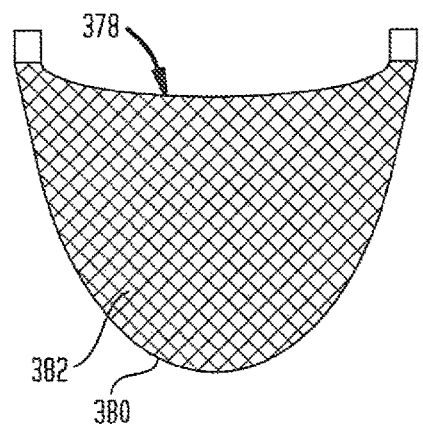
FIG. 4 is a plan view of a leaflet suitable for use with the collapsible prosthetic heart valve of FIG. 3, according to another embodiment of the present invention.

FIG. 4 illustrates a leaflet 378 according to an embodiment of the invention that may replace each of the leaflets 278 described above with reference to the prosthetic heart valve 200. The leaflet 378 may have the same function and shape as the leaflets 278.

Similar to the leaflets 140, the leaflets 378 may be made of a braided metal material, in which a metal wire, such as nitinol wire, is braided to create a flat mesh. The metal wire may have a diameter of between about 0.002 inches and about 0.020 inches. The metal wire may be arranged in a flat mesh pattern having a plurality of pores 382 between locations where the wires overlap one another. In some examples, the leaflet 378 may include a braided wire material that is not made of metal, but that has rigidity similar to that of a metal wire. Other materials may be used, but it is desirable that such materials should exhibit superelasticity in order to effectively collapse the leaflets into a delivery device. The leaflets 378 may be attached along their belly portions 380 to the cells 262 of the stent 202 of FIG. 3, with the commissure between adjacent leaflets being attached to the commissure attachment features 266. The leaflets 378 may be attached to the stent 202 and/or the cuff 276 using one or more sutures. In one embodiment, wires of the braid of each leaflet 378 may be attached to connectors (not shown) that could be coupled to the commissure attachment features 266.

Similar to the leaflets 140, the leaflets 378 may comprise two layers of braided wire with a layer of fabric between the layers of braided wire. The wire may be nitinol and the fabric may be made of a polyester material, for example. The presence of the fabric layer may help promote occlusion of the pores 382 to speed the formation of an endothelialized layer of tissue. In one embodiment, the layers of braided nitinol and the layer of fabric may be combined by placing the layer of fabric in a tube of braided nitinol, flattening the tube around the layer of fabric using heat-set forming fixtures, for example, and then trimming the nitinol/fabric assembly to the desired shape. In some examples, the leaflets 378 may include an inner layer of material that is not made of fabric, but that has flexibility similar to that of a fabric, such as a polyurethane sheet.

After the prosthetic heart valve 200 is implanted into the native valve annulus of a patient, the leaflets 378 would initially allow blood flow through the pores 382, but the leaflets may be configured such that the pores would be closed within seconds or minutes of implantation via acute clotting within the pores. Over time, this initial healing response would be converted into an endothelialized layer of tissue within the pores.

In comparison to the leaflets 278, which may be wholly or partly formed of any suitable biological material, among other materials, the leaflets 378 made of a braided metal material may have higher durability and therefore would be advantageous to use in a prosthetic heart valve that is to be implanted in a younger patient, who may have a relatively high remaining lifespan.

Figure 5:
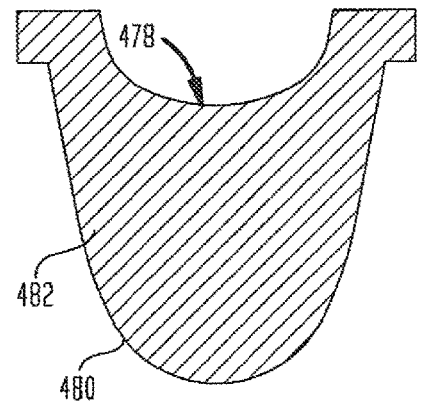
FIG. 5 is a plan view of another leaflet suitable for use with the collapsible prosthetic heart valve of FIG. 3, according to yet another embodiment of the present invention.

FIG. 5 illustrates a leaflet 478 according to an embodiment of the invention that is a variation of the leaflet 378 and that may replace each of the leaflets 278 described above with reference to the prosthetic heart valve 200.

The leaflet 478 may have the same shape as the leaflet 378, but it may have a metal wire frame 480 defining a periphery of the leaflet and a central fabric body 482 that is affixed to the frame. The metal wire frame 480 may be formed of a biocompatible metal, such as nitinol. The metal wire that comprises the frame 480 may have a diameter of between about 0.002 inches and about 0.020 inches. In some examples, the frame 480 may be formed of a braded wire material that is not made of metal, but that has rigidity similar to that of a metal wire. Other materials may be used, but it is desirable that such materials should exhibit superelasticity in order to effectively collapse the leaflets into a delivery device. The fabric body 482 may be made of a polyester material, for example. The leaflets 478 may be attached to the stent 202 and/or the cuff 276 using one or more sutures. In one example, wires of the frame 480 may be attached to connectors (not shown) that could be coupled to the commissure attachment features 266. In some examples, the body 482 may be made of a material that is not fabric, but that has flexibility similar to that of a fabric, such as a polyurethane sheet.

After the prosthetic heart valve 200 is implanted into the native valve annulus of a patient, the leaflets 478 would initially allow blood flow through pores in the fabric body 482, but the leaflets may be configured such that the pores would be closed within seconds or minutes of implantation via acute clotting within the pores. Over time, this initial healing response would be converted into an endothelialized layer of tissue within the pores and overlying the fabric body. The frame 480 may help the leaflet 478 retain its shape as tissue grows onto it, thereby preventing the leaflet from bunching in an undesirably way.

In one embodiment, the leaflets 478 may be modified to have the same shape as each of the leaflets 140 of FIG. 2A so that they may be used in the MHV 110 in place of the leaflets 140, with either the rigid frame 120 or the collapsible variation of the frame 120 that is described above.

In comparison to the leaflets 278, which may be wholly or partly formed of any suitable biological material, among other materials, the leaflets 478 made of a metal wire frame and a fabric body may have higher durability and therefore would be advantageous to use in a prosthetic heart valve that is to be implanted in a younger patient, who may have a relatively high remaining lifespan.

In summary, the disclosure herein describes multiple embodiments of a prosthetic heart valve, including surgically implanted mechanical heart valves and transcatheter heart valves. A prosthetic heart valve may include a collapsible and expandable stent having a proximal end, a distal end, an annulus section adjacent to the proximal end, and a plurality of cells connected to one another in a plurality of annular rows around the stent; a cuff attached to the annulus section of the stent; and a plurality of leaflets attached to at least one of the cuff or the stent within an interior region of the stent, the leaflets together may have a coapted position occluding the interior region of the stent and an open position in which the interior region is not occluded, each leaflet may include a flat mesh of braided metal material having a plurality of pores extending therethrough, and the leaflets may be devoid of biological material at a time of implantation; and/or the flat mesh of braided wire material may be made of nitinol wire having a diameter of between about 0.002 inches and about 0.020 inches; and/or each of the leaflets may comprise a first flat mesh of braided wire material, a second flat mesh of braided wire material, and a layer of flexible material disposed between the first flat mesh and the second flat mesh; and/or the layer of flexible material may be made of a polyester fabric; and/or the pores may be configured to be closed after implantation via an acute clotting response followed by the formation of an endothelialized layer of tissue within the pores.

Also described herein are multiple embodiments of a prosthetic heart valve that may include a collapsible and expandable stent having a proximal end, a distal end, an annulus section adjacent the proximal end, and a plurality of cells connected to one another in a plurality of annular rows around the stent; a cuff attached to the annulus section of the stent; and a plurality of leaflets attached to at least one of the cuff or the stent within an interior region of the stent, the leaflets together may have a coapted position occluding the interior region of the stent and an open position in which the interior region is not occluded, each leaflet may include a wire frame defining a periphery of the leaflet and a central flexible body affixed to the frame, the flexible body may have a plurality of pores extending therethrough, and the leaflets may be devoid of biological material at a time of implantation; and/or the wire frame may be made of nitinol wire having a diameter of between about 0.002 inches and about 0.020 inches; and/or the central flexible body may be made of a polyester fabric; and/or the pores may be configured to be closed after implantation via an acute clotting response followed by the formation of an endothelialized layer of tissue within the pores.

Further described herein are multiple embodiments of a mechanical heart valve that may include a frame defining a central opening; a sewing cuff affixed to and extending around an exterior periphery of the frame; and one or more leaflets each pivotably coupled to the frame, the leaflets together may have a closed position substantially occluding the central opening and an open position in which the central opening may not be substantially occluded, each leaflet may include a flat mesh of braided wire material having a plurality of pores extending therethrough, and the leaflets may be devoid of biological material at a time of implantation; and/or the frame may include rigid segments that are coupled to one another, and the frame and the leaflets may be configured to be collapsed and inserted into a transcatheter delivery device before the time of implantation; and/or the flat mesh of braided wire material may be made of nitinol wire having a diameter of between about 0.002 inches and about 0.020 inches; and/or each of the leaflets may include a first flat mesh of braided wire material, a second flat mesh of braided wire material, and a layer of flexible material disposed between the first flat mesh and the second flat mesh; and/or the layer of flexible material may be made of a polyester fabric; and/or the pores may be configured to be closed after implantation via an acute clotting response followed by the formation of an endothelialized layer of tissue within the pores.

Still further described herein are multiple embodiments of a mechanical heart valve that may include a frame defining a central opening; a sewing cuff affixed to and extending around an exterior periphery of the frame; and one or more leaflets each pivotably coupled to the frame, the leaflets together may have a closed position substantially occluding the central opening and an open position in which the central opening may not be substantially occluded, each leaflet may include a wire frame defining a periphery of the leaflet and a central flexible body affixed to the frame, the body may have a plurality of pores extending therethrough, and the leaflets may be devoid of biological material at a time of implantation; and/or the frame may include rigid segments that are coupled to one another, and the frame and the leaflets may be configured to be collapsed and inserted into a transcatheter delivery device before the time of implantation; and/or the wire frame may be made of nitinol wire having a diameter of between about 0.002 inches and about 0.020 inches; and/or the central flexible body may be made of a polyester fabric; and/or the pores may be configured to be closed after implantation via an acute clotting response followed by the formation of an endothelialized layer of tissue within the pores.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve, comprising:
a collapsible and expandable stent having a proximal end, a distal end, an annulus section adjacent the proximal end, and a plurality of cells connected to one another in a plurality of annular rows around the stent;
a cuff attached to the annulus section of the stent; and
a plurality of leaflets attached to at least one of the cuff or the stent within an interior region of the stent, the leaflets together having a coapted position occluding the interior region of the stent and an open position in which the interior region is not occluded, each leaflet comprising a flat mesh of braided wire material having a plurality of pores extending therethrough, the leaflets being devoid of biological material at a time of implantation in a patient.

2. The prosthetic heart valve of claim 1, wherein the flat mesh of braided wire material is made of nitinol wire having a diameter of between about 0.002 inches and about 0.020 inches.

3. The prosthetic heart valve of claim 1, wherein each of the leaflets comprises a first flat mesh of braided wire material, a second flat mesh of braided wire material, and a layer of flexible material disposed between the first flat mesh and the second flat mesh.

4. The prosthetic heart valve of claim 3, wherein the layer of flexible material comprises a polyester fabric.

5. The prosthetic heart valve of claim 1, wherein the pores are configured to be closed after implantation via an acute clotting response followed by the formation of an endothelialized layer of tissue within the pores.

6. A prosthetic heart valve, comprising:
a collapsible and expandable stent having a proximal end, a distal end, an annulus section adjacent the proximal end, and a plurality of cells connected to one another in a plurality of annular rows around the stent;
a cuff attached to the annulus section of the stent; and
a plurality of leaflets attached to at least one of the cuff or the stent within an interior region of the stent, the leaflets together having a coapted position occluding the interior region of the stent and an open position in which the interior region is not occluded, each leaflet comprising a wire frame defining a periphery of the leaflet and a central flexible body affixed to the frame, the flexible body consisting essentially of a polymer web having a plurality of pores extending therethrough, the leaflets being devoid of biological material at a time of implantation in a patient.

7. The prosthetic heart valve of claim 6, wherein the wire frame is made of nitinol wire having a diameter of between about 0.002 inches and about 0.020 inches.

8. The prosthetic heart valve of claim 6, wherein the polymer web comprises a polyester fabric.

9. The prosthetic heart valve of claim 6, wherein the pores are configured to be closed after implantation via an acute clotting response followed by the formation of an endothelialized layer of tissue within the pores.

10. A mechanical heart valve, comprising:
a frame defining a central opening;
a sewing cuff affixed to and extending around an exterior periphery of the frame; and
one or more leaflets each pivotably coupled to the frame, the leaflets together having a closed position substantially occluding the central opening and an open position in which the central opening is not substantially occluded, each leaflet comprising a flat mesh of braided wire material having a plurality of pores extending therethrough, the leaflets being devoid of biological material at a time of implantation in a patient.

11. The mechanical heart valve of claim 10, wherein the frame comprises rigid segments that are coupled to one another, and the frame and the leaflets are configured to be collapsed and inserted into a transcatheter delivery device before the time of implantation in a patient.

12. The mechanical heart valve of claim 10, wherein the flat mesh of braided wire material is made of nitinol wire having a diameter of between about 0.002 inches and about 0.020 inches.

13. The mechanical heart valve of claim 10, wherein each of the leaflets comprises a first flat mesh of braided wire material, a second flat mesh of braided wire material, and a layer of flexible material disposed between the first flat mesh and the second flat mesh.

14. The mechanical heart valve of claim 13, wherein the layer of flexible material comprises a polyester fabric.

15. The mechanical heart valve of claim 10, wherein the pores are configured to be closed after implantation via an acute clotting response followed by the formation of an endothelialized layer of tissue within the pores.

16. A mechanical heart valve, comprising:

a frame defining a central opening;

a sewing cuff affixed to and extending around an exterior periphery of the frame; and one or more leaflets each pivotably coupled to the frame, the leaflets together having a closed position substantially occluding the central opening and an open position in which the central opening is not substantially occluded, each leaflet comprising a wire frame defining a periphery of the leaflet and a central flexible body affixed to the frame, the flexible body having a plurality of pores extending therethrough, the leaflets being devoid of biological material at a time of implantation in a patient.

17. The mechanical heart valve of claim 16, wherein the frame comprises rigid segments that are coupled to one another, and the frame and the leaflets are configured to be collapsed and inserted into a transcatheter delivery device before the time of implantation in a patient.

18. The mechanical heart valve of claim 16, wherein the wire frame is made of nitinol wire having a diameter of between about 0.002 inches and about 0.020 inches.

19. The mechanical heart valve of claim 16, wherein the flexible body comprises a polyester fabric.

20. The mechanical heart valve of claim 16, wherein the pores are configured to be closed after implantation via an acute clotting response followed by the formation of an endothelialized layer of tissue within the pores.

* * * * *